United States Patent [19]

Cronin

[11] Patent Number: 4,790,848
[45] Date of Patent: Dec. 13, 1988

[54] BREAST PROSTHESIS WITH MULTIPLE LUMENS

[75] Inventor: Thomas D. Cronin, Houston, Tex.

[73] Assignee: Dow Corning Wright, Arlington, Tenn.

[21] Appl. No.: 125,856

[22] Filed: Nov. 27, 1987

[51] Int. Cl.$^4$ .............................................. A61F 2/12
[52] U.S. Cl. ......................................................... 623/8
[58] Field of Search ........................... 623/7, 8, 10, 11

[56] References Cited

U.S. PATENT DOCUMENTS

| 4,125,117 | 2/1978 | Lee | 623/7 |
| 4,298,998 | 11/1981 | Nacify | 623/8 |
| 4,433,440 | 2/1984 | Cohen | 623/8 |
| 4,455,691 | 6/1984 | Van Aken Redinger | 623/8 |

Primary Examiner—Richard J. Apley
Assistant Examiner—David J. Isabella
Attorney, Agent, or Firm—Allan O. Maki

[57] ABSTRACT

This invention provides a multiple lumen implant in which the inner lumen is of a substantially spherical shape and is unattached or free-floating. The invention provides a construction which is able to provide and maintain a high projection and to simulate the natural flow of breast tissue during a variety of activities in which the patient may participate on a daily basis.

8 Claims, 1 Drawing Sheet

BREAST PROSTHESIS WITH MULTIPLE LUMENS

BACKGROUND OF THE INVENTION

This invention relates to improved breast prostheses suitable for implantation in a human breast for reconstructive or cosmetic purposes.

Surgical reconstruction of human breasts as a result of injury or as a result of partial or total mastectomy has been performed for many years. Various surgical prostheses have been developed for implantation in the human breast as a part of breast reconstruction or augmentation. See for example my U.S. Pat. No. 3,293,663. The ability of a physician to offer a patient who has undergone a mastectomy a lifelike substitute for the breast which has been removed is an important element in the rehabilitation of the patient.

A major problem with prostheses heretofore used is the lack of maintained projection, particularly in a manner such that the proper shape and location on the chest wall would be achieved and maintained, and the fact that their shape and consistency generally does not match the remaining breast. In an effort to overcome said problems a number of types of implants have been proposed. See for example, U.S. Pat. No. 4,650,487 to Chaglassian in which a high projection implant was proposed by utilizing two shells or lumens in which the inner lumen is secured to the rear wall of the outer lumen and in which the material contained in the inner lumen is of a higher density than that contained in the outer lumen. There is no disclosure in said patent, however, of a construction in which the inner lumen is unattached and free to move within the outer lumen so as to provide a prosthesis which closely simulates the natural flow of breast tissue during daily activities.

Another proposed solution to this problem is disclosed in U.S. Pat. No. 4,636,213 in which a prosthesis is proposed which is provided with valves so that additional fluid can be introduced into the prosthesis by means of an injection needle. This patent likewise does not teach the use of a prosthesis in which an unattached inner lumen is provided. If implants utilizing an attached inner lumen for maintaining projection are not positioned correctly during surgery the projection which is provided is not in an optimum position on the patient.

Canadian Pat. No. 1,059,262 discloses an external breast prosthesis. Such external prostheses are simply attached over the chest area of the patient and may be removed at night if desired. The prosthesis shown in said patent includes a silicone or other filler such as glycerin in which a bag of air is inserted to reduce its weight. There is no disclosure, in said patent, however, of an unattached fluid filled envelope designed to simulate the natural flow of tissue within a human breast.

A silicone gel-saline implant utilizing an inner, silicone gel filled lumen which is unattached within an outer lumen which is filled by the surgeon with a saline solution has been marketed by Dow Corning Wright Corporation of Arlington, Tn. See their sales literature identified as Form No. L080-0101. Such commercially available implants have, however, heretofore always employed an inner lumen which was of the same shape (generally a flattened cushion or dome shape having a flattened rear side) having a height and diameter nearly as great as that of the outer lumen. The inner lumen in such constructions was therefore not motile except to a very limited degree, and did not serve to provide or maintain the projection of the implant.

SUMMARY OF THE INVENTION

One of the objects of this invention is to provide a multiple lumen implant in which the inner lumen is of a substantially spherical shape and is unattached or free-floating. The invention provides a construction which is able to simulate the natural flow of breast tissue during a variety of activities in which the patient may participate on a daily basis in a manner which was hithertofore unobtainable.

The principal object of the invention is to overcome the disadvantages of prior art implants and provide an implant which not only is relatively soft, provides a high projection and maintains its shape, resembling that of natural tissue, but also maintains its projection during the course of daily activities such as standing up or lying down.

These and other objects of the invention are achieved by providing a surgically implantable multilumen mammary implant comprising an outer flexible lumen having a broad base and exterior configuration capable of approximating the contour of a human breast, the lumen being filled with a soft fluid material which also contains an unattached, motile inner lumen of a substantially spherical shape.

Preferably the motile unattached inner lumen occupies from 25% to 60% of the volume of the prosthesis. Constructions within said range have been found to yield the desired results of this invention. The novel composite construction of the present invention thus includes a broad based outer lumen of a relatively low profiled dome or somewhat teardrop shape which contains a fluid, preferably a silicone polymeric gel material, within which is an unattached, substantially spherically shaped inner lumen of envelope capable of readily moving therein and of a size and shape that creates and maintains a high, natural appearing projection with flow characteristics resembling that of natural breast tissue.

BRIEF DESCRIPTION OF THE DRAWINGS

These and other objects and advantages of the invention will become apparent from the following detailed description when taken in conjunction with the accompanying drawings wherein.

DETAILED DESCRIPTION

Figure 1:
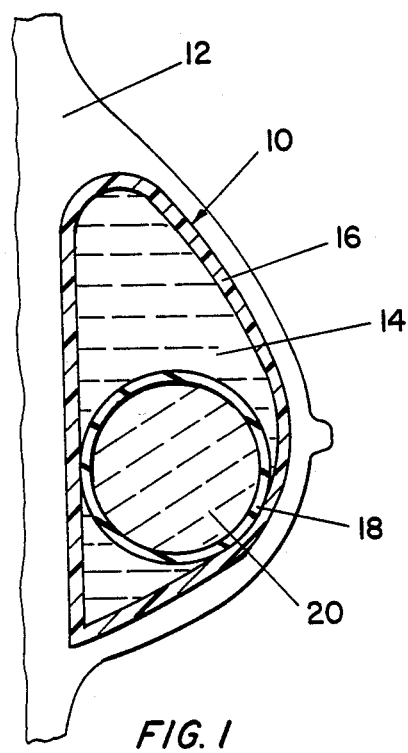
FIG. 1 is a schematic cross-sectional view of a human breast which has been surgically implanted with a mammary prosthesis in accordance with this invention; and, FIG. 2 is a cross-sectional view of a trilumen mammary prosthesis made in accordance with the invention.

Referring more specifically to the drawings, there is seen in FIG. 1 a breast prosthesis generally indicated by numeral 10 implanted within the breast tissue 12 of a patient. The implant includes a silicone gel or similar fluid material 14 contained within outer envelope 16. Envelope 16 is of a relatively broad based shape, being relatively flat on the rear or lower surface 17 and semi-rounded or dome shaped on the forward or upper surface 19. It will be apparent to those skilled in the art that the outer lumen may be of a somewhat teardrop shape or other shape that is nonsymetrical but designed to conform to the contours of the human breast. Unattachedly disposed within and motile therein is an inner envelope or lumen 18, of a substantially spherical shape which contains fluid material 20. Substantially spherical inner lumen 18 is of a diameter substantially less than that of the base diameter of outer lumen 16, but large enough to equal or exceed the major portion of the height or thickness of said outer lumen. Inner lumen 18 also contains a fluid, preferably a silicone gel, which substantially fills its entire volume. Because the inner lumen 18 is substantially filled to its entire volume and because its diameter either meets or exceeds the normal height of outer lumen 16, lumen 18 provides and maintains the desired projection to the prosthesis.

Figure 2:
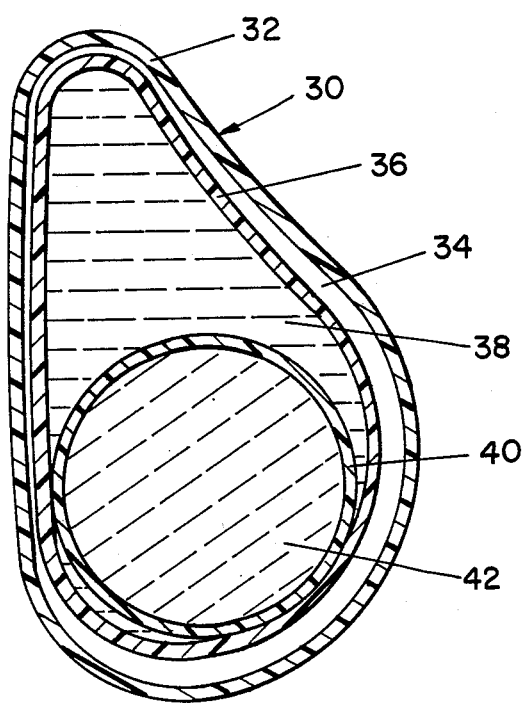

A further embodiment of the invention is shown in FIG. 2 which illustrates a trilumen implant indicated generally by numeral 30. Implant 30 includes an outer envelope 32 containing a fluid 34 contained between the walls of envelope 32 and the outer wall of a second envelope or lumen 36. A second gel or similar fluid material 38 is contained in envelope 36. An inner unattached substantially spherically shaped inner lumen or envelope 40 contains a third fluid or gel material 42. The outer wall of lumen 36 may be either smooth or textured and desired.

By "substantially spherical" as the term is used herein is meant the shape of the envelope either is spherical or nearly enough spherical to permit free movement or motility of the inner envelope in all directions. Thus, while slightly flattened spheres or somewhat elliptically shaped envelopes could be employed, such distortions should be of a relatively minor degree so as not to impede the free movement of the lumen within the fluid contained in the outer lumen. The fluids or gels contained in the inner and outer lumens should be of a relatively similar density so that the free floating inner lumen will not rise or sink unduly. It will be apparent, however, that the density of the fluid in the unattached lumen could be slightly greater than that of the outer lumen, if desired. The term "fluid" as used herein is intended to include not only liquid materials such as saline solutions sometimes used in mammary prostheses, but also gel or gel type materials which are relatively cohesive and which tend to flow only when pressure is exerted thereon. Thus "fluid" is intended to include materials exhibiting any type of flow behavior.

Because the inner envelope of the present invention is unattached and motile, prostheses formed in accordance with the present invention are better able to simulate the properties and natural flow of breast tissue. For example, when the patient lies on her back the unattached inner unit, because of its substantially spherical shape, will move to the side, in a manner simulating the normal flow of natural breast tissue. Such flow simulation is apparently achieved because of the fact that when external pressure or a natural force such as gravity is applied to the prosthesis, the fluid in the outer lumen will move, thus repositioning the projection-maintaining, motile inner lumen.

The walls of the lumens may be constructed of any soft flexible biocompatible (commonly referred to as "medical grade") materials such as silicone elastomers. The primary criteria for the walls are that they are durable, biologically compactible, soft, pliable and capable of assuming natural body contours. Preferred materials are silicone elastomers such as polydimethylsiloxane or polymethylvinylsiloxane or copolymers thereof with other substances. Other materials such as polyurethanes or other polymers can be substituted, as will be apparent to those skilled in the art. Such materials as well as silicone gel materials used as fluids within the lumens are well known to those skilled in the art and are commercially available. The outer wall of lumen 16 or lumen 36 may be either smooth or textured and desired, as is known to those skilled in the art.

It is preferred to construct the prosthesis of the present invention by utilizing a barrier layer of a composition which impedes the tendency of the silicone gel to bleed or migrate through the walls of the envelopes. Such barrier layers generally contain a fluorine-containing organopolysiloxane such as 3,3,3-triflouropropylmethylpolysiloxane, but other materials known in the art may be employed for that purpose. Such layers are preferably contained between the silicone elastomer layers forming the envelopes, especially the outer envelope. Alternatively the barrier layer could be applied on the surfaces of the envelopes, most particularly the inner surfaces of the outer envelope. Specific examples of such barrier layers and compositions are set forth in Larson Canadian Pat. No. 1,199,451 and in U.S. Pat. No. 4,455,691.

It is to be understood that the foregoing embodiments are to be considered illustrative of the invention. Various modifications, changes or alterations of the invention disclosed herein may be evident to those skilled in the art and thus the invention disclosed herein is not intended to be limited by the description hereinabove but rather, is intended to be limited only by the appended claims.

What is claimed is:

1. A multi-lumen mammary prosthesis for surgical implantation comprising:
    an outer, closed, broad-based flexible envelope of medical grade elastomer containing a first fluid material,
    an unattached second, closed, flexible envelope contained in said first fluid material and being motile therewithin, said second envelope being substantially spherical in shape and containing a second fluid material, the diameter of said substantially spherical envelope being sufficient to maintain outward projection of the prosthesis.

2. A prosthesis according to claim 1 wherein said second envelope is spherically shaped.

3. A prosthesis according to claim 1 wherein said second envelope occupies between 25% and 60% of the volume of said prosthesis.

4. A prosthesis according to claim 1 wherein said first envelope is formed from a silicone elastomer.

5. A prosthesis according to claim 1 wherein each of said fluids is a silicone gel.

6. A prosthesis according to claim 1 wherein said second envelope is contained within and motile within a third, fluid containing envelope which is contained within said first envelope.

7. A multi-lumen mammary prosthesis for surgical implantation comprising:
    an outer closed broad- based flexible envelope of medical grade silicone elastomer containing a silicon gel material,
    an unattached second closed flexible silicone elastomer envelope contained in said gel material and being motile therewithin, said second envelope being substantially spherical in shape and also containing a silicone gel material, the diameter of said substantially spherical envelope being sufficient to provide and maintain outward projection of the prosthesis.

8. A prosthesis according to claim 7 wherein at least the outermost envelope is formed of wall materials which impede the migration of silicone gel materials through said walls.

* * * * *